US010114097B2

(12) United States Patent
Benner et al.

(10) Patent No.: US 10,114,097 B2
(45) Date of Patent: Oct. 30, 2018

(54) MEDICAL IMAGING APPARATUS HAVING MULTIPLE SUBSYSTEMS, AND OPERATING METHOD THEREFOR

(71) Applicant: Siemens Aktiengesellschaft, Munich (DE)

(72) Inventors: Thomas Benner, Erlangen (DE); Swen Campagna, Engelthal (DE); Thorsten Feiweier, Poxdorf (DE); Bernd Kuehn, Uttenreuth (DE); Thorsten Speckner, Erlangen (DE); Peter Speier, Erlangen (DE); Daniel Nico Splitthoff, Erlangen (DE); Michael Wullenweber, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 451 days.

(21) Appl. No.: 14/870,032

(22) Filed: Sep. 30, 2015

(65) Prior Publication Data

US 2016/0091587 A1    Mar. 31, 2016

(30) Foreign Application Priority Data

Sep. 30, 2014    (DE) .................. 10 2014 219 779

(51) Int. Cl.
*G01R 33/54*      (2006.01)
*A61B 5/055*      (2006.01)
(Continued)

(52) U.S. Cl.
CPC ........... *G01R 33/543* (2013.01); *A61B 5/055* (2013.01); *G01R 33/3875* (2013.01); *G01R 33/4833* (2013.01)

(58) Field of Classification Search
CPC ............ G01R 33/543; G01R 33/54; G01R 33/56375; G01R 33/56383;
(Continued)

(56) References Cited

U.S. PATENT DOCUMENTS 6,515,478 B1    2/2003   Wicklow et al.
7,218,113 B2    5/2007   Feiweier et al.
(Continued)

OTHER PUBLICATIONS

De Graaf et al., "Dynamic Shim Updating (DSU) for Multi-Slice Signal Acquisition," Proc. Intel. Soc. Mag. Reson. Med., vol. 10 (2002).
(Continued)

*Primary Examiner* — Clayton E Laballe
*Assistant Examiner* — Ruifeng Pu
(74) *Attorney, Agent, or Firm* — Schiff Hardin LLP

(57) ABSTRACT

In a method for operating a medical imaging examination apparatus having multiple subsystems, current ambient conditions in a scan volume of the apparatus are determined and stored in a global ambient condition parameter set. A control computer starts a scan sequence according to a selected scan protocol, and sequence control data that define different functional sub-sequences for the respective subsystems are provided to the control computer. Different effective volumes are assigned to each functional sub-sequence, and respective current sub-regions in the effective volume associated with the respective sub-sequence are determined, in which a volume optimization is to take place. Control signals for the scan sequence are calculated using the sequence control data, the global ambient condition parameter set, and the determined current sub-regions of the affected volumes, in order to optimize the functional sub-sequences at least with regard to the current sub-region of the assigned effective volume.

10 Claims, 6 Drawing Sheets

(51) Int. Cl.
  *G01R 33/483* (2006.01)
  *G01R 33/3875* (2006.01)

(58) Field of Classification Search
  CPC .................. G01R 33/4835; G01R 33/546;
          G01R 33/243; G01R 33/246; G01R
          33/3875; G01R 33/1833; G01R 33/561;
          G01R 33/5612; G01R 33/5617; G01R
          33/5635; G01R 33/5659; A61B 5/055
  See application file for complete search history.

(56) References Cited

U.S. PATENT DOCUMENTS

| | | | |
|---|---|---|---|
| 8,111,069 B2 | 2/2012 | Feiweier | |
| 9,557,248 B2* | 1/2017 | Feiweier | G01M 99/008 |
| 2003/0191386 A1* | 10/2003 | Heid | G01R 33/54 600/410 |
| 2005/0189940 A1* | 9/2005 | Feiweier | G01R 33/543 324/307 |
| 2007/0170917 A1 | 7/2007 | Thompson et al. | |
| 2008/0180104 A1* | 7/2008 | Furudate | G01R 33/54 324/318 |
| 2008/0272787 A1 | 11/2008 | Boskamp et al. | |
| 2009/0309595 A1* | 12/2009 | Yatsui | A61B 5/0555 324/309 |
| 2010/0182007 A1* | 7/2010 | Dornhaus | G01R 33/243 324/309 |
| 2010/0286802 A1* | 11/2010 | Feiweier | G01R 33/54 700/90 |
| 2011/0052031 A1* | 3/2011 | Feiweier | G01R 33/56518 382/131 |
| 2011/0163749 A1 | 7/2011 | Katscher et al. | |
| 2011/0172515 A1 | 7/2011 | Fautz et al. | |
| 2012/0217966 A1 | 8/2012 | Feiweier | |
| 2012/0249137 A1 | 10/2012 | Witschey et al. | |
| 2013/0039549 A1* | 2/2013 | Muller | G01R 33/543 382/128 |
| 2015/0362574 A1 | 12/2015 | Wu et al. | |
| 2016/0091584 A1* | 3/2016 | Feiweier | G01R 33/543 324/309 |
| 2016/0091586 A1* | 3/2016 | Benner | G01R 33/543 324/322 |
| 2016/0091587 A1* | 3/2016 | Benner | G01R 33/543 324/322 |
| 2016/0091588 A1* | 3/2016 | Benner | G01R 33/543 324/309 |
| 2016/0091590 A1* | 3/2016 | Benner | G01R 33/56527 324/309 |

OTHER PUBLICATIONS

Meier et al., "Concomitant Field Terms for Asymmetric Gradient Coils: Consequences for Diffusion, Flow, and Echo-Planar Imaging," Magnetic Resonance in Medicine, vol. 60, pp. 128-134 (2008).

* cited by examiner

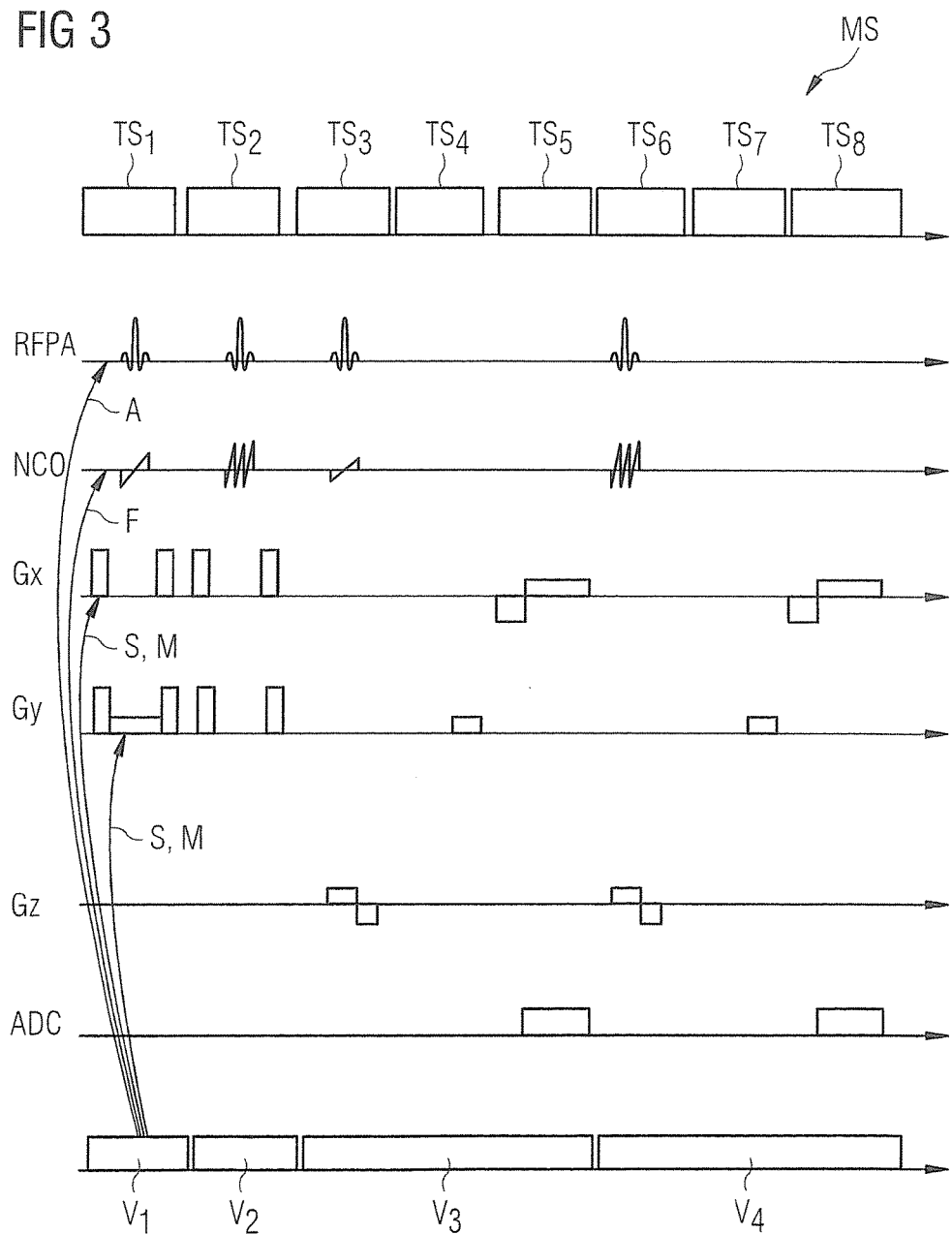

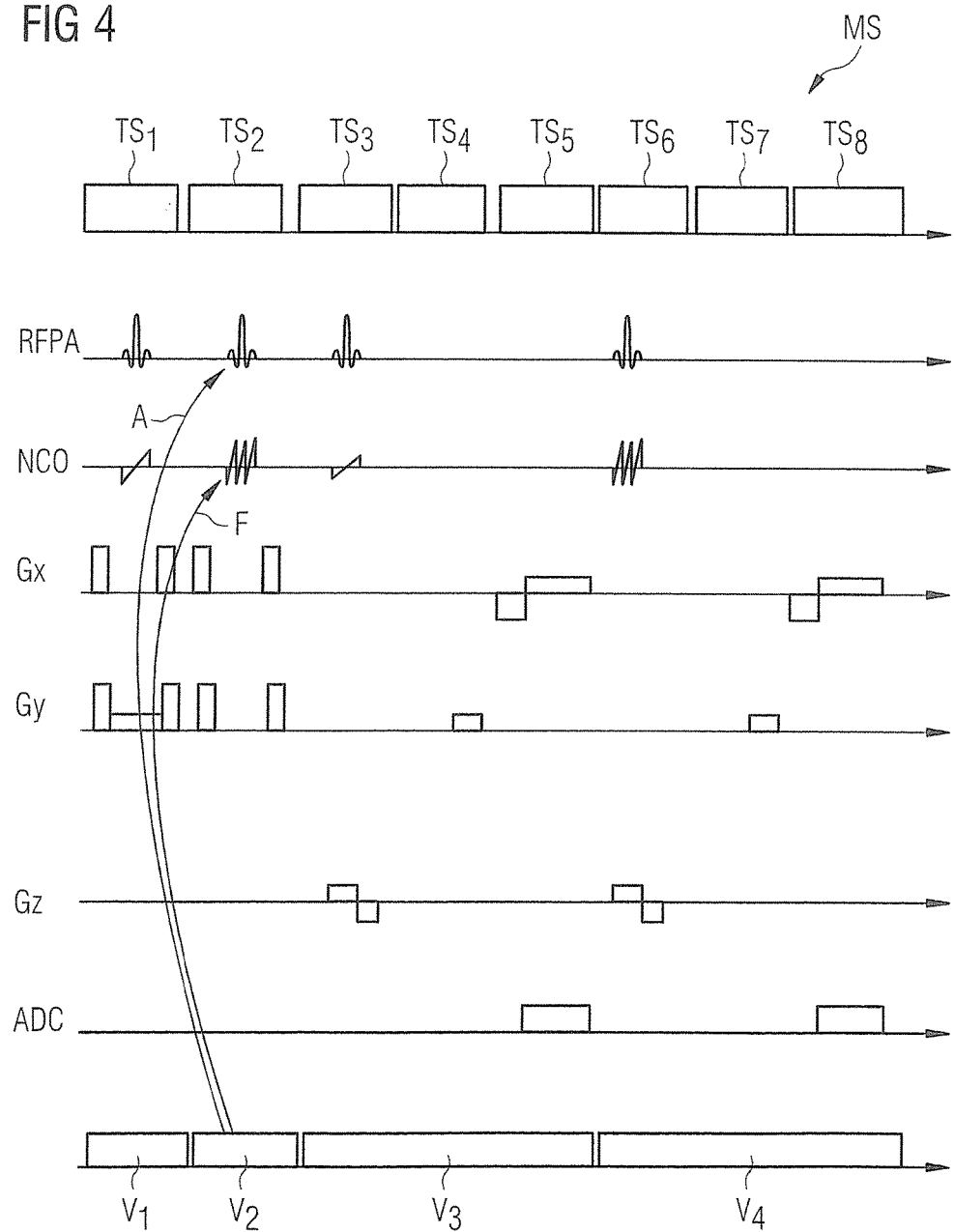

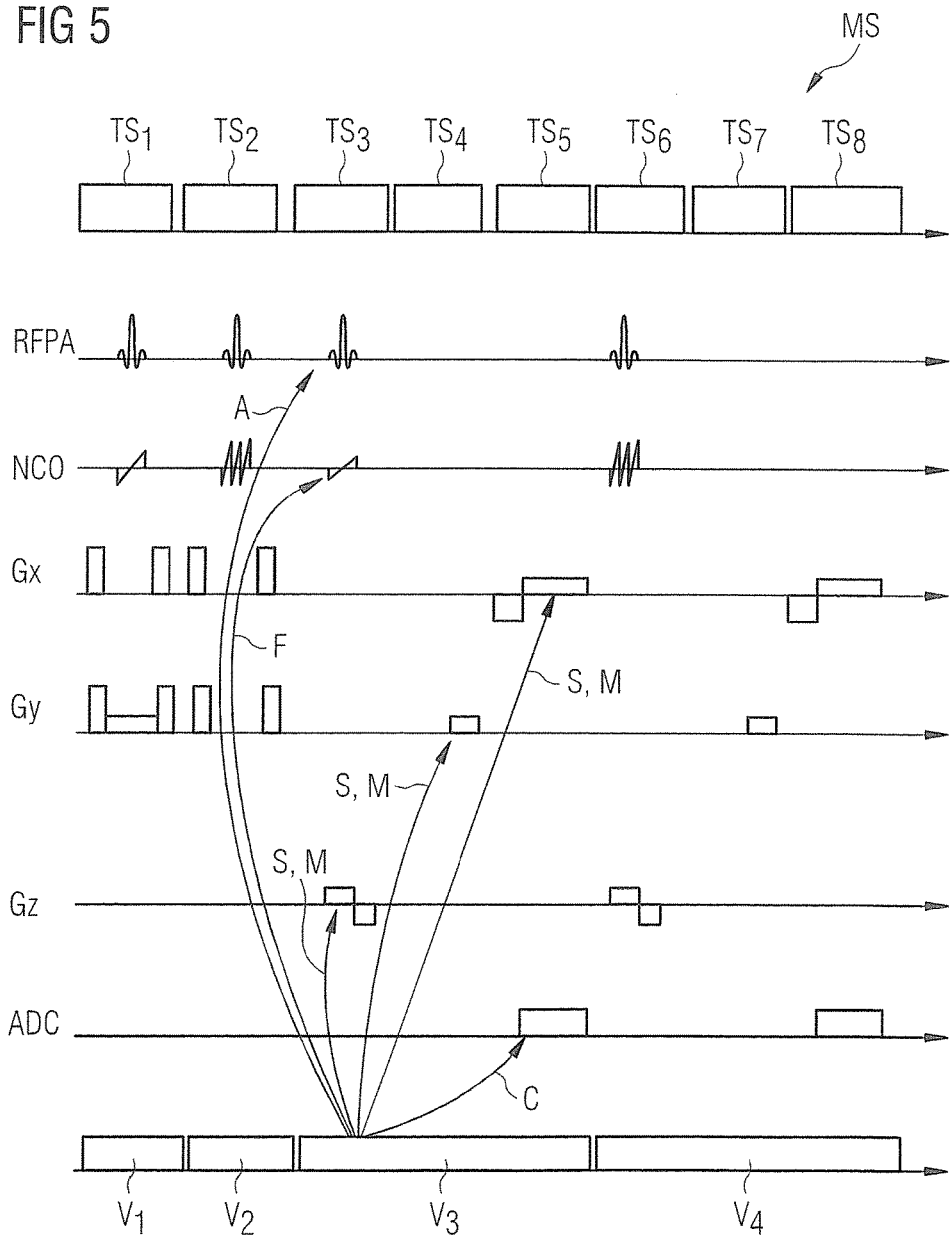

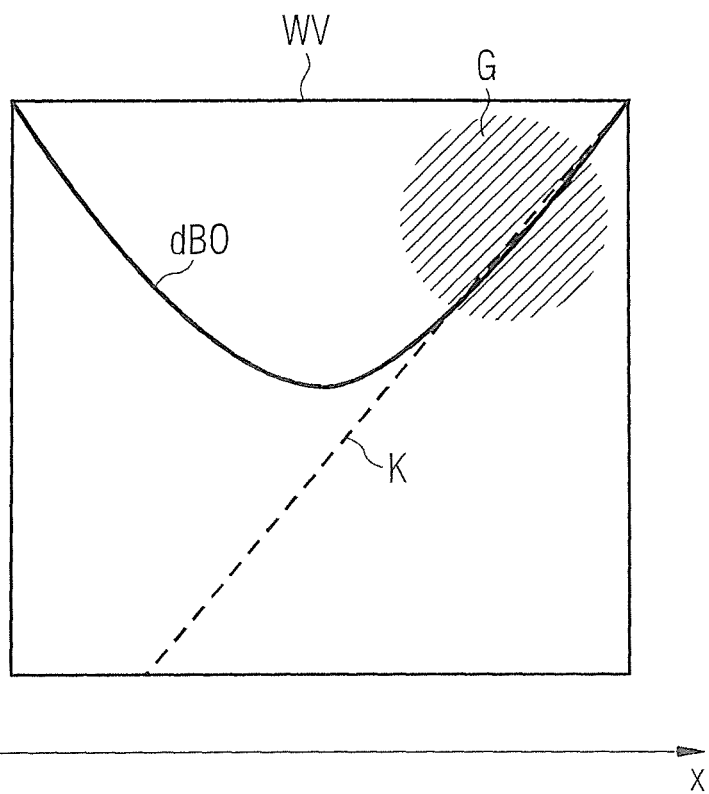

MEDICAL IMAGING APPARATUS HAVING MULTIPLE SUBSYSTEMS, AND OPERATING METHOD THEREFOR

BACKGROUND OF THE INVENTION

Field of the Invention

The invention concerns to the operation of a medical imaging examination apparatus having multiple subsystems, a corresponding medical imaging examination apparatus, and an associated electronically readable data carrier encoded with programming instructions for implementing such a method.

Description of the Prior Art

Medical imaging examination apparatuses such as magnetic resonance apparatuses and computed tomography apparatuses are complex systems with a large number of technical subsystems. These include, in a magnetic resonance apparatus, a basic field magnet system, a gradient system, a shim system and a radio frequency transmission system as well as a radio frequency receiving system.

In order to generate images or spectroscopic data from an examination object with a magnetic resonance apparatus, the examination object is positioned in the scanner in a strong homogeneous basic magnetic field, also known as the $B_0$ field, generated by the basic field magnet system with a field strength of 0.2 Tesla to 7 Tesla or more, so that the nuclear spins in the object align along the basic magnetic field direction. In order to trigger nuclear spin resonance, radio frequency excitation signals (RF pulses) are radiated into the examination object with suitable antennas of the radio frequency transmission system, so that the nuclear spin of particular atoms stimulated to resonance by this radio frequency field are tilted through a particular flip angle relative to the magnetic field lines of the basic magnetic field. The nuclear spin resonance that is triggered, i.e. the radio frequency signals (also "magnetic resonance signals") emitted during the precession of the nuclear spin are detected by the radio frequency receiving system, typically digitized, and normally stored as complex number values (if a spatial reference is given) in a "k-space matrix" as "k-space data". For example, in single-voxel spectroscopy scans (without spatial reference), the digitized data are stored as complex time signals, also known as "FID data". On the basis of the k-space data or FID data, MR images can be reconstructed or spectroscopic data can be determined. For spatial encoding of the scan data, rapidly switched magnetic gradient fields are overlaid on the basic magnetic field by the gradient system. The shim system is intended to homogenize the magnetic fields.

All these technical modules must be suitably operated in a coordinated way by a control system. The adjustment and switching of the individual subsystems necessary for a particular imaging process must be undertaken by the control system at the right time point in each case. Typically, the volume to be imaged within an imaging sequence is recorded in subvolumes, for example, in 2-D imaging, in multiple slices or, in 3-D imaging, in multiple "slabs". The subvolumes recorded in this way are then assembled into an overall volume. A further definition of subvolumes can be given as "regions of interest" (ROI) or "volumes of interest" (VOI) defined, for example, by the operator. Furthermore, in magnetic resonance systems, additional subvolumes arise when determining local saturation regions or local preparation or labeling pulses.

As mentioned above, sequence control data are transmitted to the control device for coordinated control, typically based on a "scan protocol". These sequence control data define different functional sub-sequences of a complete scan sequence. In a magnetic resonance recording, for example, a first sub-sequence may be a pulse sequence in order to achieve a saturation locally in a particular region. Further sub-sequences can contain, for example, particular preparation pulses and yet further sub-sequences serve for successive excitation and for receiving the magnetic resonance signals in different slices or slabs.

Typical methods based on MR technology, such as tomographic imaging (MRT—magnetic resonance tomography) or spectroscopy (MRS—magnetic resonance spectroscopy) require "benign" ambient physical conditions in order to ensure the best possible quality in the data recorded. For example, this relates to the spatial homogeneity, temporal stability and the absolute accuracy of the relevant magnetic fields and radio frequency fields, that is, the basic magnetic field ($B_0$) and the gradient and radio frequency fields ($B_1$).

Conventionally, deviations from ideal ambient conditions can at least partially be compensated for, for example, by system-specific settings known as "tune-ups", in particular with regard to eddy current-induced dynamic field disruptions or gradient sensitivities or by examination object-specific settings, particularly in relation to susceptibility-related static field disruptions or spatial variations of the radio frequency field. However, the compensation settings specified before the beginning of a scan conventionally remain valid throughout the entire scan ("static" adjustment).

For spatially variable ambient conditions that cannot be entirely compensated, this entails a compromise for data quality.

De Graaf et al. describe in "Dynamic Shim Updating (DSU) for Multi-Slice Signal Acquisition", Proc. Intl. Soc. Mag. Reson. Med. 10, p. 536, 2002, a rudimentary form of a dynamic adjustment of the shim currents of the field coils for the B0 shim in functional multi-slice MR imaging. For this purpose, a firm field determination sequence is created for determining spatial field changes of first or higher orders which must be exactly matched to the corresponding parameters (e.g. slice positions and orientations) of the desired imaging sequence. The field determination sequence records the data necessary for field determination and analyzes them in order to calculate optimized shim currents (of first or higher order) therefrom for each slice to be scanned with the imaging sequence. Subsequently, the imaging sequence is started with the optimized shim currents. The user needs to watch very closely for consistency between the imaging sequence and the field determination sequence since, otherwise, inconsistencies can lead to a worsening of the image quality. Therefore, for each imaging sequence and each change of such a sequence, a new field determination sequence must be created and carried out before the scan with the imaging sequence. These methods are therefore very complex and difficult for the user to combine with other, for example static, adjustments since interactions between different parameters cannot be taken into account or only to a limited extent. If statically adjusted parameters are changed, this can have effects on the optimum dynamic settings of the shim currents and a new field determination sequence and calculation of the optimized shim currents would have to be carried out. Furthermore, the optimization is restricted to the slices of the imaging sequence. Smaller volumes, for example, regional saturation volumes are not taken into account here.

In DE 10 2009 020 661 B4 also, a method is described with which parameters of a scan sequence, for example, within magnetic resonance technology can be adapted at the run time of the scan sequence. Furthermore, it is described therein that different functional sub-sequences are typically associated with different effective volumes. I.e. for each sub-sequence, a different subvolume of the overall scan volume is relevant. Due to the determination of the parameters at run time, it can however occur that, in the time available which is limited due to the already running scan sequence, no useful parameters can be determined. In this event, either the scan as a whole can be terminated or sub-optimum, static parameters can be utilized.

SUMMARY OF THE INVENTION

An object of the present invention is to provide a method for the operation of a medical imaging examination apparatus that has multiple subsystems, and a control computer that controls the subsystems in a coordinated manner in order to carry out a scan sequence, a medical imaging examination apparatus and an associated electronically readable data carrier, which enable reliable adaptation of sequence control data to existing ambient conditions (adjustment) in a user-friendly and time-optimized manner and overcomes the above-mentioned disadvantages of conventional methods.

The invention is based, inter alia, on the insight that for scans in which the volume of the examination object relevant for the signal excitation and the data reception changes during the scan, the quality of the data can be significantly improved by a dynamic optimization of the compensation settings for the currently relevant volumes. This applies, for example, for two-dimensional multi-slice imaging, multi-voxel spectroscopy (e.g. in conjunction with successive localized excitation) or on use of diverse magnetization preparations (e.g. fat suppression, regional saturation, inversion, markings, etc.).

This object is achieved by a method according to the invention for the operation of a medical imaging examination apparatus having multiple subsystems and a control computer that controls the subsystems in a coordinated manner in order to carry out a scan sequence has the following steps:

Current ambient conditions in the scan volume of the medical imaging examination apparatus are determined in the control computer.

The current ambient conditions are stored in a global ambient condition parameter set, with the parameters of the ambient condition parameter set describing the ambient conditions.

The control computer starts a scan sequence according to (using) scan protocol that has been selected.

Sequence control data that are relevant for the selected scan protocol, which define different functional sub-sequences for the respective subsystems, of the scan sequence belonging to the scan protocol are provided to the control computer.

Different effective volumes are assigned by the control computer to each functional sub-sequence.

Respective current sub-regions in the effective volume associated with the respective current functional sub-sequence of the scan sequence are determined in which effective volume an optimization is to take place.

Control signals for the scan sequence are calculated in the control computer on the basis of the sequence control data, the global ambient condition parameter set, and the determined respective current sub-regions of the effective volumes such that the functional sub-sequences of the scan sequence are locally optimized at least with regard to the current sub-region of their assigned effective volume. The control computer makes these control signals available in electronic form for operating the medical imaging examination apparatus.

The method according to the invention enables flexible reaction to any changes in the scan conditions at run time and optimum compensation parameters to be determined in each case and to be set by the control signals for the scan. At the same time, changes to the ambient conditions and changes, such as position changes of the sub-regions to be optimized of the effective volumes can be taken into account, so that a particularly high degree of flexibility of the method can be achieved.

Restriction in a targeted manner to sub-regions in a volume of interest the examination object thus is possible, which has a positive effect on the computation time and on the quality of the examination results. Because of the improved possibilities for adapting the control signals, it is also possible to build less expensive hardware into the medical imaging examination apparatus, which can then be manufactured more economically, because any sub-optimum ambient conditions due to the hardware can be compensated with the inventive method.

If, with the method described, weightings are taken into account in the effective volumes (e.g. regarding the tissue contents), regions which are otherwise difficult to optimize, e.g. for optimization volumes with signal contributions only in the peripheral region, can be optimized particularly well in order to improve the image quality.

In the inventive method, it is not necessary, as in the prior art, for a user to ensure the consistency of different scan protocols, for example, protocols for adjustment scans for determining ambient conditions and from the actual scan. Rather, established adjustment scans can be used without a user having to parameterize them first.

A medical imaging examination apparatus according to the invention with multiple subsystems has a control computer configured to implement the method according to the invention, wherein the control computer is configured to control the subsystems in a coordinated manner for executing a scan sequence on the basis of sequence control data, wherein the sequence control data define various functional sub-sequences of the scan sequence with which different effective volumes are associated.

A non-transitory, electronically readable data carrier according to the invention has electronically readable control information (programming instructions) stored thereon, so that, when the data carrier is loaded in a control computer of a medical imaging examination apparatus, the programming instructions cause the control computer to implement the method according to the invention.

The advantages and details described above with respect to the method apply to the medical imaging examination apparatus, and the electronically readable data carrier.

BRIEF DESCRIPTION OF THE DRAWINGS

FIG. 3 is a simplified exemplary embodiment of a scan sequence with multiple sub-sequences and their associated effective volumes, with a representation of the parameters for the individual subsystems optimized for the first sub-sequence to the first effective volume.

FIG. 4 shows the scan sequence with the individual sub-sequences and associated effective volumes as in FIG. 3, but with a representation of the parameters of the subsystems optimized for the second sub-sequence to the second effective volume.

FIG. 5 shows the scan sequence with the individual sub-sequences and associated effective volumes as in FIG. 3, but with a representation of the parameters of the subsystems optimized for the third effective volume.

FIG. 6 schematically illustrates the method according to the invention.

DESCRIPTION OF THE PREFERRED EMBODIMENTS

Figure 1:
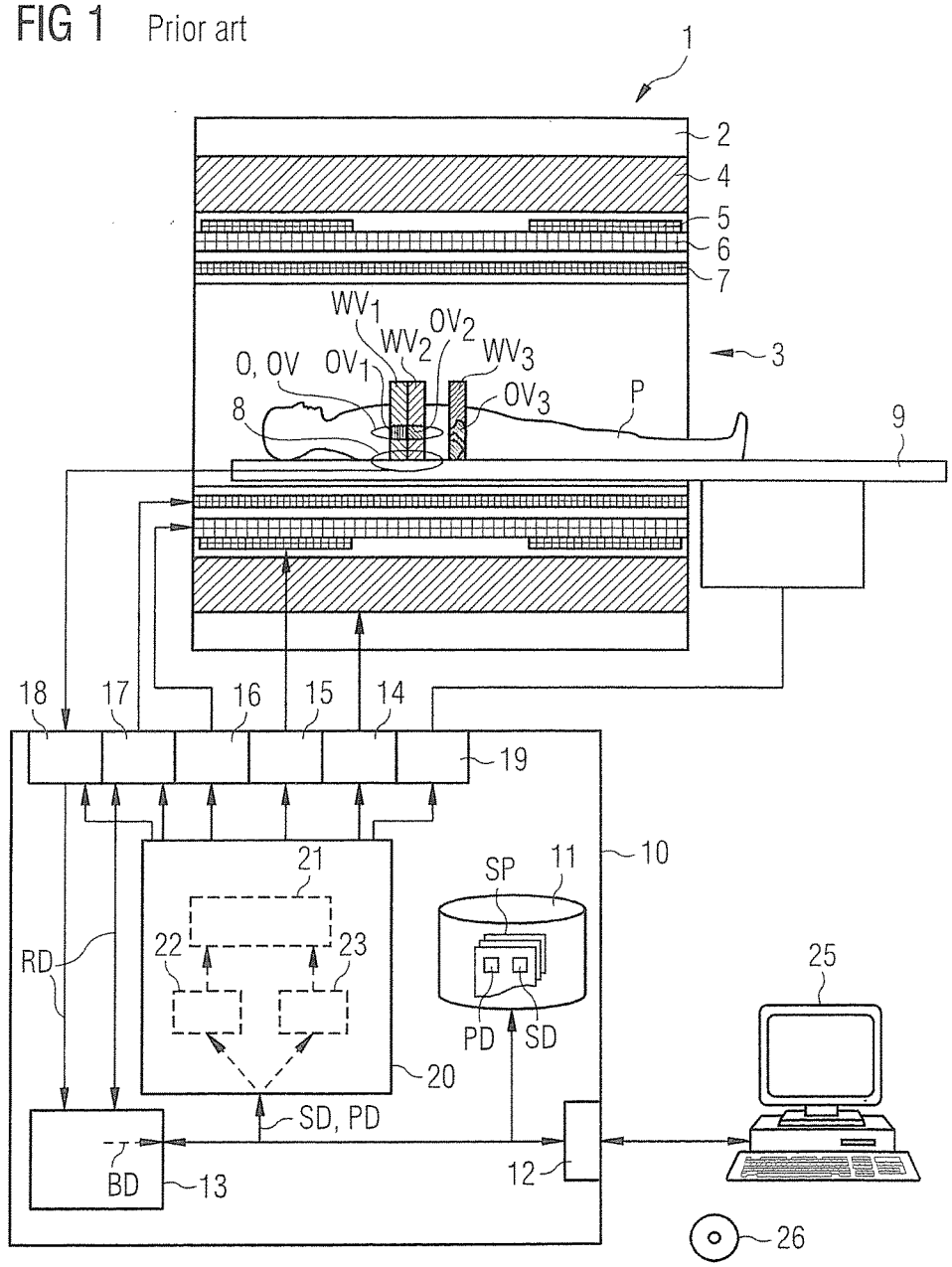
FIG. 1 schematically illustrates a known medical imaging examination apparatus in the form of a magnetic resonance apparatus that can implement the invention.

FIG. 1 shows a basic schematic form of a medical imaging examination apparatus 1 that although the basic components are known, can be configured according to the invention. The apparatus includes the actual magnetic resonance scanner 2 with an examination space 3 or patient tunnel situated therein. A table 9 can be moved into this patient tunnel 3 through various positions so that an examination object, e.g. a patient P or test subject lying thereon can be placed during an examination at a particular position within the magnetic resonance scanner 2 relative to the magnetic system and the radio frequency system arranged therein and is also displaceable between different positions during a scan. It should be mentioned at this point that the exact construction of the magnetic resonance scanner 2 is not essential. Thus, for example, a cylindrical system with a typical patient tunnel can be used, but also a C-arm-shaped magnetic resonance device which is open at one side.

Basic components of the magnetic resonance scanner 2 are a basic field magnet 4, a number of shim coils 5 and magnetic field gradient coils 6 as well as a whole-body radio frequency coil 7. The reception of magnetic resonance signals induced in the examination object can take place by the whole body coil 7, with which typically the radio frequency signals for inducing the magnetic resonance signals are also emitted. It is also possible to receive these signals, for example, with local coils 8 placed on or under the patient. All of these components are known to those skilled in the art and are shown only schematically in FIG. 1.

The individual components are controlled by a control computer 10, which is shown here in the form of a combined block. This can be a control computer that can be composed of a number of individual computers, possibly spatially separated and connected to one another by suitable cables or the like. This control computer 10 is connected, via a terminal interface 12, to a terminal 25, via which an operator can control the entire system 1. The terminal interface 12 should be understood as meaning any connection of input devices, such as a mouse and/or keyboard, and display devices, for example, a screen or monitor of the terminal 25 to the control computer 10.

This control computer 10 has, inter alia, a basic magnetic field control apparatus 14 that monitors the cooling of the basic field magnet, a shim coil control apparatus 15, and a gradient coil control apparatus 16. The whole body coil 7 is controlled by a radio frequency transmission/receiving unit 17. The radio frequency transmitting/receiving unit 17 has, for example, a radio frequency pulse amplifier for amplification and shaping of the radio frequency pulses and an NCO with which the frequency and phase position of the radio frequency pulses can be stipulated. With a further radio frequency receiving unit 18, signals detected by local coils 8 are read out. This radio frequency receiving unit (processor) 18 can include, for example, a coil selection unit in order to select the relevant local coil from among multiple local coils that are available, and an NCO for setting the frequency and phase position. A patient table control unit 19 serves to control the table 9.

The basic field magnet 4, together with its control apparatus 14, the basic magnetic field system 4, 14, the shim coils 5 together with the associated control apparatus 15, the shim system 5, 15, the magnetic field gradient coils 6 with the associated control apparatus 16, the gradient system 6, 16, the radio frequency coils 7 together with their radio frequency transmission/receiving unit 17, form a radio frequency transmission/receiving system 7, 17 and the local coils 8 together with their radio frequency receiving unit 18 form a further radio frequency receiving system 8, 18.

All the control apparatuses 14, 15, 16, 19 and the radio frequency transmitting and/or receiving units 17, 18 are controlled in a coordinated manner by a central control computer 20 so that the basic magnetic fields, gradient fields and radio frequency pulses required for the execution of a scan are output-synchronized, the shim coils are correctly set and the table 9 is in the correct position. Furthermore, it must be ensured that, at the relevant time point, the signals are read out at the local coils 8 by the radio frequency receiving unit 18 and any signals at the whole body coil 7 are read out by the radio frequency transmitting/receiving unit 17 and further processed in an appropriate manner.

The signals or raw data RD acquired in this way are then passed on to an image reconstruction unit 13 in which the desired magnetic resonance image data or spectroscopic data BD are reconstructed in order then to present them on the screen of the terminal 25 or to store them in a memory 11.

The magnetic resonance scanner 2 of this type and the associated control computer 10 also have or can have a number of further components that will not be discussed in detail herein. For example, the examination apparatus 1 can be coupled, via a suitable interface, to a network, for example, a radiological information system (RIS) in order to receive control protocols that can be used in the apparatus 1 or, for example, to transmit magnetic resonance images generated by the apparatus 1, to save them in external mass storage units or to transfer them to diagnosis stations or printers or the like.

The generation of the control signals for the individual control apparatuses 14, 15, 16, 19 and the radio frequency transmitting and/or receiving units 18, 17 by the central control computer 20 is accomplished via a control signal generating module 21, realized in the form of software, in a processor of the control computer 10 that generates the control signals ST on the basis of sequence control data SD that define the different sub-sequences of the complete scan sequence. An example of a scan sequence composed of multiple sub-sequences will be described below with reference to FIGS. 3 to 5. The sequence control data SD are typically set within control protocols SP that characterize the scan protocol of the scan to be carried out and can be stored for the apparatus 1 in a memory 11. A control protocol SP of this type contains all the control data necessary for the smooth execution of a particular scan sequence. The operator can select a protocol of this type SP for a scan to be carried out, by a suitable user interface via the terminal 25 and then have the scan performed fully automatically on the basis of this control protocol SP. However, it is also possible for the operator to call and modify a control protocol SP in order to carry out specific scans. It is also possible to select control protocols SP via a further network interface (not shown) on other computers, particularly from the manufacturer of the magnetic resonance system or made available by specialist service providers involved in the development of control protocols.

As described in detail above, it is useful for the achievement of the best possible image quality if the individual subsystems are controlled for a particular sub-sequence such that they are optimized to the effective volume essential for the particular sub-sequence or a particular part thereof. This has conventionally been achieved by the developer of a control protocol making account, in advance, of which effective volume is relevant for which sub-sequence, and then accordingly modifying the sequence control data or the parameters for the subsystems in the control protocol, so that with the sub-sequence, optimization is achieved in the defined effective volume.

The method described herein can also exist in the form of a computer program that implements the method on a control computer 10 when it is carried out on the control computer 10. An electronically readable data carrier 26 with electronically readable control information stored thereon can also be provided, the control information including at least one computer program written thereon and being configured such that, upon loading of the data carrier 26 into a control computer 10 of a medical imaging examination apparatus 1, the control information carries out a method as described.

Figure 2:
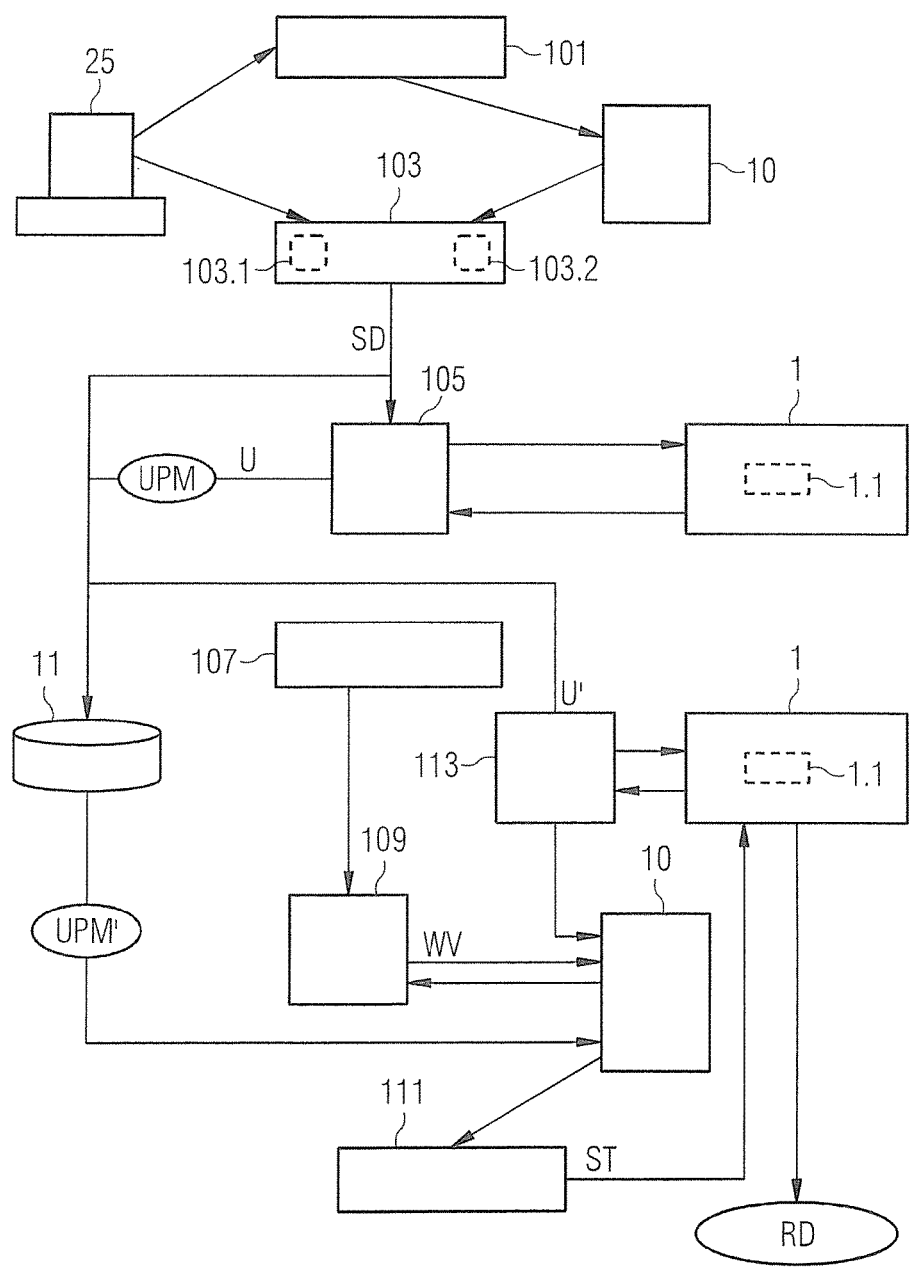
FIG. 2 is a flowchart illustrating the method according to the invention.

FIG. 2 shows a method according to the invention for the operation of a medical imaging examination apparatus having multiple subsystems and a control computer 10 that controls the subsystems in a coordinated manner in order to carry out a scan sequence.

Before the start of a scan to be performed on a patient P or other examination object, first in a step 105, current ambient conditions U, preferably in the entirety of the scan volume of the medical imaging examination apparatus 1 (i.e., the scanner thereof) are determined and are stored in a global ambient parameter set UPM in the memory 11. The parameters of ambient condition parameter set UPM describe the ambient conditions U in an appropriate manner. The ambient conditions U can be determined directly by the scanner of the medical examination apparatus 1, such as navigator signals. Alternatively, suitable external sensors 1.1 that measure, for example, the basic magnetic field $B_0$ and/or the radio-frequency field $B_1$.

The global ambient condition parameter set is stored, preferably spatially resolved, in the form of three-dimensional parameter maps that represent the ambient conditions.

In an exemplary embodiment, a weighting is associated with each of the parameters contained in the global ambient condition parameter set UPM. This weighting can represent the tissue content, such as which tissue is present where, in a spatially resolved manner.

The ambient condition parameter set UPM can include, for example, the values of the local basic magnetic field $B_0$ and/or the values of the local radio-frequency field $B_1$, e.g. in amplitude and phase. The values of the local radio-frequency field $B_1$ can be provided respectively for each element of an RF transmission array used.

The stored ambient condition parameter set UPM contains all information needed to determine optimized adjustment parameters, and thus optimized control signals for the scan sequence, for any desired subvolumes of the scan volume of the medical examination apparatus 1. Using the global ambient condition parameter set UPM as the data base, it is possible, for all types of changes during the scan, particularly changes due to position changes in the examination object, to compensate for these changes rapidly and flexibly during the scan.

Furthermore, before the start of a scan to be performed on a patient P or other examination object, in a step 101, before or after the setting of the ambient condition parameter set UPM, the control protocol assigned for a scan sequence that is to be carried out is provided to the control computer 10. For this purpose, inputs can be made by a user at the terminal 25 of the medical imaging examination device 1, e.g. a specific control protocol selected and/or adjusted according to current wishes, as described above.

In a further step 103, the sequence control data SD of relevance for the transferred control protocol, which define different functional sub-sequences of a scan sequence belonging to the control protocol, are determined and stored in the memory unit 11. Depending on the type of scan desired, which specifies, for example, the sequence type, further scan parameters and a body region to be examined, namely, the control protocol, may be useful for a different selection of sequence control data, e.g. for a dynamic adaptation. For example, it may be desired that the scan be relatively insensitive to variations in the $B_1$ field, in order to simplify the sequence of the subsequent scan, the corresponding sequence control data SD, for example, a transmitter scaling for the flip angle setting or $B_1$ shim settings, are designated as sequence control data SD (step 103.1) to be set statically, while other sequence control data concerning, for example, the $B_0$ field are designated as sequence control data SD (step 103.2) to be adapted dynamically. In this way, the robustness of the method can be improved and the scope of the scans to be carried out for determining the ambient conditions can be reduced.

Furthermore, before the scan, specific sequence control data SD, preliminary optimization parameters on the basis of currently known effective volumes, and currently known ambient conditions can be determined and effectively used as orientation quantities, or as starting values, for the optimized control signals ST to be determined in step 111.

Additionally or alternatively, the determined sequence control data SD can include limit values to be adhered to for the optimized control signals ST to be determined in step 111. When these limit values are adhered to, the executability of the scan is ensured. The executability of the scan depends particularly on limit values to be adhered to regarding the hardware that is used, such as, for example, maximum gradient power outputs and/or safety-related limit values to be adhered to, for example, a maximum SAR-loading (SAR=Specific Absorption Rate).

In this way, it can be ensured that the scan can be carried out despite the optimization of the control signals ST according to the invention carried out during the run time of the scan.

In a step 107, the actual scan is started and takes place by means of a selected scan protocol.

If the sequence control data that are relevant for the selected scan protocol which define different functional sub-sequences of a scan sequence belonging to the scan protocol, have not been provided before the start of the scan (block 107), then this can also take place (block 103) after the start of the scan (block 107).

Provided the effective volumes do not change during the scan, they can be stipulated before the start of the scan and associated with each functional sub-sequence of the scan sequence. For scans in which the effective volumes do change during the scan, different effective volumes VW can only be associated with each functional sub-sequence of the scan sequence once the scan is running. The assignment of the effective volumes to the functional sub-sequences of the scan sequence is shown in block 109. On an assignment during the scan, as described above, in each case, a current sub-region is determined in the effective volume VW associated with the respective current functional sub-sequence of the scan sequence in which an optimization of the control signals is to take place, particularly to compensate for inhomogeneities. In a simple exemplary embodiment, a current effective volume corresponds to the sub-region in which the optimization is to take place.

This can be done automatically on the basis of the control protocol. For a desired multi-slice scan, each slice to be recorded can define a volume of this type. Another example is a regional saturation volume pre-determined by the control protocol. This will be discussed below in relation to FIGS. 3 to 5.

The determination of the current sub-regions in which an optimization of the control signals is to take place can be implemented, for example, on the basis of stored weighting information of the ambient condition parameter set UPM. Furthermore, a direct or an indirect manipulation of the sub-regions to be optimized can be provided by the user. For example, during the provision of sequence control data SD before the start of the scan, the user can specify volumes as optimization volumes (e.g. "volumes of interest") that include, for example, the anatomical region of interest in each case. The respective effective volumes WV that are always currently determined during the scan can then each be restricted to the sub-region of the overlap of themselves with the applicable optimization volume. Thus, the method according to the invention enables optimization for any desired sub-regions of the effective volume and is not restricted, for example, to the effective volumes pre-determined by the scan, as in the case of slices in multi-slice scans.

The determination of the respective current sub-regions in the effective volume WV associated with the respective current functional sub-sequence of the scan sequence can take account herein of a possible position change of an examination object, e.g. a patient situated in the scan volume of the medical imaging diagnostic device. This can be done, for example, automatically by the medical examination apparatus 1 together with the control computer 10, for example, on the basis of the current scan instructions or the current scan sequence. In this regard, the changes in the position of the examination object can be determined from manipulations made by a user during interactive scans such as, for instance, in fluoroscopic scans, or from a determined slice re-positioning by an active movement correction (e.g. on the basis of navigator scans or external sensors 1.1) during the scan, or the like. It is also possible for the position changes to be determined solely on the basis of data determined by external sensors 1.1. Optical sensors such as cameras, in conjunction with methods for quantifying a movement, particularly of rigid bodies, are examples of such external sensors 1.1.

In a step 111, control signals ST for the scan sequence are calculated by the control computer 10 on the basis of the provided sequence control data SD, the global ambient condition parameter set UPM, and the determined respective current sub-regions of the effective volumes WV by executing an algorithm wherein the functional sub-sequences of the scan sequence are locally optimized at least with regard to the current sub-region of their assigned effective volume.

Additionally, in a step 113, the ambient conditions can be monitored. For this purpose, changes in the ambient conditions U', particularly in the scan volume of the medical imaging diagnostic device 1, can be detected during the scan. The detected changes can also be stored. The ambient condition parameter set UPM can be corrected on the basis of the changes detected, so that a corrected ambient condition parameter set UPM' is obtained.

The control computer 10 thus accesses respective updated ambient parameter sets UPM' during the scan and can determine respective optimum control signals ST with which the ongoing scan is further controlled.

The control signals ST control the scanner of the medical imaging examination apparatus 1, which thereby generates raw data RD that can be stored in the memory 11 or reconstructed as image data or spectroscopic data and, if required, displayed.

Thus, for example, in step 105 an ambient condition parameter set UPM is recorded and stored for the whole scan volume and contains, for each location x, e.g. with a resolution of 4 mm×4 mm×4 mm or coarser or finer depending on the application, the local basic magnetic field $B_0$ and a weighting, in the simplest case, e.g. for each location $W(x)=1$ if tissue is present and $W(x)=0$ if no tissue is present. If, at run time of the scan in step 111, control signals ST are determined which optimize the RF center frequency and the gradient offset streams (to compensate for static 0th and 1st order field disruptions), so that within the current relevant sub-region, for example a cuboid, the image quality is maximized, for each location x within the relevant sub-region of the current effective volume, the value for the local basic magnetic field $B_0(x)$ and the respective associated weighting parameter $W(x)$ are read out. On this basis, a weighted basic magnetic field average value $B_0'$ and a weighted main field gradient G' are determined, from which a corresponding RF center frequency and a corresponding shim offset current for compensation, which are used by the control signal during the scan, are calculated.

In another example, in step 105 an ambient condition parameter set UPM is recorded and stored for the entire scan volume and contains, for each location x, e.g. with a resolution of 4 mm×4 mm×4 mm or coarser or finer depending on the application, for each RF transmission channel used, the local radio-frequency field $B_1$ e.g. in amplitude and phase and a weighting $W(x)$ for each location. In the simplest case $W(x)=1$ if tissue is present and $W(x)=0$ if no tissue is present. If, at run time of the scan in step 111, control signals ST are determined that optimize the RF scaling factor and the RF power distribution (to compensate for static spatial $B_1$ variations). For each location x within the relevant sub-region of the current effective volume, the value for the local radio-frequency field $B_1(x)$ and the respective associated weighting parameter $W(x)$ are read out. The current relevant sub-region may be a cuboid, and the optimization may be to maximize image quality. On this basis, a weighted radio-frequency field average value $B_1'$, and a weighted development of the spatial distribution are determined according to the basic functions of the RF fields generated by the transmission channels. From these basic functions RF amplitude scaling factor and a corresponding RF power distribution for compensation, which are used by the control signal during the scan, are calculated.

A more complex weighting can be used that, for example, weights different tissues to differing extents.

Nevertheless, the central control computer 20 of the control computer 10 can include, apart from a control signal generating module 21, a sequence control data determining module 22 that recognizes and reads out the sequence control data SD within a control protocol SP. In addition, the central control computer 20 preferably includes a position data determination module 23 that recognizes the effective volume position data PD in the control protocol SP, and the thereby obtained sequence control data and position data are then processed in a suitable manner by the control signal generating module 21 in order to achieve the desired optimization. In principle, the sequence control data determination module 22 and the position data determination module 23 can also be realized as a combined module which recognizes the sequence control data SD and the effective volume position data PD and transfers them to the control signal generating module 21. Furthermore, the sequence control data determination module and the position data determination module can also be integrated into the control signal generating module 21. In FIG. 1, however, a separate representation of these modules was selected in order to make clear that the optimization for the effective volumes associated with the individual sub-sequences of the scan sequence only takes place fully automatically in the central control computer 20.

The position data calculation device 23 can also be configured so that it determines a restricted optimization volume for individual sub-sequences, for example, on the basis of effective volume position data PD obtained and image data DB generated with the use of the reconstruction unit 13 in previous scout scans.

An example of when this is useful is also shown schematically in FIG. 1 on the patient P in the patient tunnel 3. Shown here are three different slices for which particular sub-sequences are to be carried out within a scan sequence. Each of these slices has a quite particular effective volume $WV_1$, $WV_2$, $WV_3$, wherein however, only part of this volume actually includes part of the patient P to be examined. Regions in this effective volume $WV_1$, $WV_2$, $WV_3$ outside the patient's body do not contain any essential image information. It is therefore useful to use as the optimization volume only the sub-region of the effective volume $WV_1$, $WV_2$, $WV_3$ which overlaps the body of the patient P. In the case of the third slice $WV_3$, this optimization volume $OV_3$ is the whole region which results as the overlap between the effective volume $WV_3$ and the volume of the patient's body.

Based on the other two effective volumes $WV_1$, $WV_2$, a further variant is shown. It is herein assumed that a particular organ O is to be examined as the examination object O within the body of the patient P. This organ O has a particular object volume OV. Since only this volume OV is of interest, the overlap of the object volume OV with the effective volumes $WV_1$, $WV_2$ is formed in order to find the respective optimization volumes $OV_1$, $OV_2$. If the case should arise that an effective volume does not have any overlap with an associated optimization volume, for example, the formation of the overlap can be dispensed with and only the effective volume considered or the optimization volume for the associated effective volume having no overlap with the optimization volume can be extrapolated as the new optimization volume to be taken as the basis. A case of this type could arise, for example, if the slices provided for the scan are larger than the VOI stipulated by the user or are larger than the organ to be imaged.

With reference to FIGS. 3 to 5, the possibilities for optimizing the individual subsystems to an effective volume associated with a particular sub-sequence will now be described, again using an actual but highly simplified scan sequence MS.

In the uppermost line, various sub-sequences $TS_1$, $TS_2$, ..., $TS_8$ are named, in each case in the form of individual blocks. Shown in the bottom line are the effective volumes $V_1$, $V_2$, $V_3$, $V_4$ associated with these sub-sequences $TS_1$, $TS_2$, ..., $TS_8$ of the scan sequence MS.

It is apparent that the first sub-sequence $TS_1$ is associated with a first effective volume $V_1$ and the second sub-sequence $TS_2$ is associated with a second effective volume $V_2$. A common effective volume $V_3$ is associated with the sub-sequences $TS_3$, $TS_4$, $TS_5$. Also, an effective volume $V_4$ is associated with the sub-sequences $TS_6$, $TS_7$, $TS_8$.

Shown between the bottom and upper lines, each on separate time lines for the individual sub-sequences, are the pulses to be output by the subsystems. I.e. by the synchronous output of the pulses, each shown beneath the sub-sequences $TS_1$, $TS_2$, ..., $TS_8$ marked by the blocks or the setting of the corresponding parameters at the subsystems, the individual sub-sequences $TS_1$, $TS_2$, ..., $TS_8$ are carried out. In the second to top line, the radio frequency pulse forms and amplitudes to be output by the radio frequency pulse amplifier RFPA are shown symbolically. In the second line, the NCO phase to be set in each case is symbolized, wherein the gradient of the curve symbolizes the frequency size. In the following lines, the gradient pulses Gx, Gy, Gz are shown and in the last but one line, the readout windows in which an analogue/digital converter ADC for reading out a selected receiving coil is controlled. For the sake of simplicity, a single-channel transmitting system is represented here. In multi-channel systems, for example, for every transmitting element, the RF pulse sequence (amplitude and/or phase) could look different in order to realize the B1 shim.

The first sub-sequence $TS_1$ of the scan sequence MS serves here for regional saturation, i.e. all the nuclei within a regionally limited effective volume $V_1$ are saturated. For this purpose, initially for dephasing, short intensive Gx and Gy gradients are switched. Subsequently, a radio frequency pulse of a particular form and amplitude with a particular temporally variable phase sequence output by the NCO is emitted, the rise of said pulse corresponding to the frequency of the radio frequency pulse, whilst simultaneously for slice selection, a further Gy gradient pulse is emitted. This sub-sequence concludes with a further short intensive gradient pulse in the x- and y-directions for dephasing.

With regard to the effective volume $V_1$, different parameters can be optimized automatically by the control device, since this effective volume $V_1$ is known. Firstly, the amplitude A of the radio frequency pulse to be emitted and simultaneously also the frequency F which is output by the NCO are optimized. In addition, for example, the shim offset currents S for the gradient coils Gx, Gy are suitably set and equally suitable parameters for a Maxwell correction M can also be transferred. The parameters locally optimized depending on the respective effective volume $V_1$ are shown in FIG. 3 with arrows starting from the bottom line and from the first volume $V_1$.

A further sub-sequence $TS_2$, which directly adjoins the first sub-sequence $TS_1$, is a chemical saturation, for example, a fat saturation. This takes place very similarly to the regional saturation by emitting a radio frequency pulse at a particular amplitude and a frequency pre-determined by the NCO, wherein here the frequency is higher than with the regional saturation in the sub-sequence $TS_1$. Here also, before the emission of the radio frequency pulse and after the emission of the radio frequency pulse, in each case, only the dephasing pulse is switched in the Gx and Gy gradient. The emission of a Gy gradient for slice selection (as in the first sub-sequence $TS_1$) does not take place since the saturation is to take place globally, i.e. the effective volume $V_2$ is here the whole volume in the scanning space. FIG. 4 shows how, for example, in this sub-sequence $TS_2$, the amplitude A and the frequency F are optimized for the current effective volume $V_2$.

Following this chemical saturation $TS_2$, the actual recording of raw data then takes place for a first slice by means of three sub-sequences $TS_3$, $TS_4$, $TS_5$, which must all act on the relevant slice. This slice determines the associated effective volume $V_3$. The first sub-sequence $TS_3$ serves for slice excitation in the effective volume $V_3$. This is achieved by emitting a radio frequency pulse RF with a particular amplitude and a frequency pre-set by the NCO with simultaneous emission of a Gz slice gradient pulse and a subsequent shorter, negative Gz rephasing pulse. The next sub-sequence $TS_4$ serves for phase encoding. For this purpose, merely a Gy gradient pulse is switched. In the subsequent sub-sequence $TS_5$, the reading out of the magnetic resonance signals generated in the effective volume $V_3$ takes place in that initially a negative Gx gradient pulse is emitted for dephasing and subsequently a positive Gx gradient pulse is emitted for rephasing, wherein simultaneously, the ADC is activated for reading out. Thereafter, the scanning of this slice is ended. Optimizable parameters are shown again in FIG. 5 by arrows: the amplitude A of the emitted radio frequency pulse, the phase and frequency F of the NCO set on output of the radio frequency pulse, and again the parameters for the shim offset S and the Maxwell correction parameters M on switching the gradient pulses Gx, Gy, Gz, respectively. With regard to the ADC, an optimization can be carried out in that—provided different readout coils (e.g. a number of local coils) are available—the best coil combination is selected for the relevant effective volume $V_3$, and this is symbolized by the coil selection parameter C.

Subsequently to the sub-sequence $TS_5$ with which the data are read out of the volume $V_3$, excitation of a further slice can take place within the sub-sequence $TS_6$. This further slice is represented here by the effective volume $V_4$. In the same way as for the first slice, i.e. for the effective volume $V_3$, in order to determine the image data also for the effective volume $V_4$, a sub-sequence $TS_7$ for phase encoding and a further sub-sequence $TS_8$ for reading out the slice are carried out.

It is clear that, in the same manner, further slices can be read out, wherein corresponding sub-sequences must be repeated. Similarly, in any desired manner, including between the scanning out of slices, further saturation sub-sequences or other special sub-sequences can be inserted, for example, to label or mark blood or other fluids, the flow of which in the body is to be determined later. According to the multiple highly varied possible sub-sequences and associated effective volumes, there arise also the most varied of possibilities for optimizing parameters of the different sub-systems for the individual sub-sequences in view of the associated effective volumes.

FIG. 6 shows a schematic representation illustrating the mode of action of the method according to the invention.

FIG. 6 shows an isocentric effective volume WV, for example, a slice to be scanned in which tissue G is present only at the right-hand upper edge. During the scan, a spatial change $dB_0$ of the basic magnetic field $B_0$ can occur due, for example, to thermal drift effects. In the representation, the spatial change $dB_0$ of the basic magnetic field $B_0$ has an approximately quadratic dependence on the location x (shown with a continuous line). Even if the medical examination device 1 can only correct changes of the basic magnetic field $B_0$ of the 0th and 1st order, for example, by pre-sets from the hardware, that is, the RF center frequency and the gradient offset current, it is still possible with the method described herein to achieve good compensation of the drift by using the weightings, as described. Since by means of the weighting information, the relevant regions of an effective volume (or a sub-region to be optimized of the effective volume) are implicitly known. It is thus possible, at run time, to determine locally optimum compensation settings K automatically (shown with the dashed line) which minimize the spatial errors in the region of the tissue G and thus control the scan by means of the control signals such that optimum scan results can be achieved.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a medical imaging examination apparatus comprising a plurality of apparatus subsystems, comprising:
   determining ambient conditions of a scan volume in a medical imaging examination apparatus;
   storing the current ambient conditions in a global ambient condition parameter set comprising parameters that describe said current ambient conditions;
   providing a selected scan protocol to control computer that is assigned to a scan sequence in which said control computer will control the plurality of apparatus subsystems in coordination to conduct the scan sequence to acquire medical imaging data from an examination subject;
   starting a scan with the selected scan protocol;
   providing said control computer with sequence control data for said selected scan protocol that define different functional sub-sequences of said scan sequence to be performed respectively by said apparatus subsystems;
   before or during said scan, in said control computer, assigning respectively different effective volumes of the examination subject to the respective functional sub-sequences;
   before or during said scan, in said control computer, determining respective current sub-regions in respective effective volumes individually associated with the respective current functional sub-sequences of the scan sequence, in which sub-regions an optimization is to be made during said scan;
   in said control computer, calculating optimized control signals for said selected scan sequence during said scan dependent on said sequence control data, the determined sub-regions of the effective volumes, and the global ambient condition parameter set, by executing an algorithm in said control computer that optimizes the functional sub-sequences locally in the examination subject at least with regard to a sub-region of the respective effective volumes; and
   in said control computer, providing said optimized control signals to at least one of said apparatus subsystems during said scan.

2. A method as claimed in claim 1 comprising storing said parameters in said ambient condition parameter set in a spatially resolved manner.

3. A method as claimed in claim 1 comprising, in said control computer, associating a weighting with each of said parameters in said global ambient condition parameter set.

4. A method as claimed in claim 3 comprising selecting said weighting from the group consisting of spatially-dependent weightings and tissue-dependent weightings.

5. A method as claimed in claim 1 comprising determining the respective current sub-regions in a respective effective volume associated with a respective current functional sub-sequence dependent on a possible position change of the examination subject in the scan volume.

6. A method as claimed in claim 1 comprising, during said scan, determining changes of said ambient conditions, and correcting said global ambient condition parameter set dependent on said changes.

7. A method as claimed in claim 1 comprising storing, as said parameters in said global ambient condition parameter set, parameters selected from the group consisting of a local magnitude of a basic magnetic field in said medical examination apparatus, an amplitude of a radio-frequency field in said medical examination apparatus, and a phase of a radio-frequency field in said medical examination apparatus.

8. A method as claimed in claim 1 comprising determining said sequence control data from the group consisting of preliminary optimization parameters that ensure that the scan can be executed with the determined control signals, and limit values that ensure that the scan can be executed with the determined control signals.

9. A medical imaging apparatus comprising:
a plurality of apparatus subsystems;
a control computer configured to determine ambient conditions of a scan volume in a medical imaging examination apparatus;
a memory in which said control computer is configured to store the current ambient conditions in a global ambient condition parameter set comprising parameters that describe said current ambient conditions;
said control computer being configured to receive a selected scan protocol that is assigned to a scan sequence in which said control computer is configured to control the plurality of apparatus subsystems in coordination to conduct the scan sequence to acquire medical imaging data from an examination subject;
said control computer being configured to start a scan with said selected scan protocol;
said control computer being configured to receive sequence control data for said selected scan protocol that define different functional sub-sequences of said scan sequence to be performed respectively by said apparatus subsystems;
said control computer being configured to assign, before or during said scan, respectively different effective volumes of the examination subject to the respective functional sub-sequences;
said control computer being configured to determine, before or during said scan, respective current sub-regions in respective effective volumes individually associated with the respective current functional sub-sequences of the scan sequence, in which sub-regions an optimization is to be made during said scan;
said control computer being configured to calculate optimized control signals for said selected scan sequence dependent on said sequence control data, the determined sub-regions of the effective volumes, and the global ambient condition parameter set, by executing an algorithm that optimizes the functional sub-sequences locally in the examination subject at least with regard to a sub-region of the respective effective volumes; and
said control computer being configured to provide said optimized control signals to at least one of said apparatus subsystems during said scan.

10. A non-transitory, computer-readable data storage medium encoded with programming instructions, said storage medium being loaded into a control computer of a medical imaging examination apparatus comprising a plurality of apparatus systems, said programming instructions causing said control computer to:
determine ambient conditions of a scan volume in a medical imaging examination apparatus;
store the current ambient conditions in a global ambient condition parameter set comprising parameters that describe said current ambient conditions;
receive a selected scan protocol that is assigned to a scan sequence in which said control computer will control the plurality of apparatus subsystems in coordination to conduct the scan sequence to acquire medical imaging data from an examination subject;
start a scan with said selected scan protocol;
receive sequence control data for said selected scan protocol that define different functional sub-sequences of said scan sequence to be performed respectively by said apparatus subsystems;
before or during said scan, assign respectively different effective volumes of the examination subject to the respective functional sub-sequences;
before or during said scan, determine respective current sub-regions in respective effective volumes individually associated with the respective current functional sub-sequences of the scan sequence, in which sub-regions an optimization is to be made during said scan;
calculate optimized control signals for said selected scan sequence dependent on said sequence control data, the determined sub-regions of the effective volumes, and the global ambient condition parameter set, by executing an algorithm in said control computer that optimizes the functional sub-sequences locally in the examination subject at least with regard to a sub-region of the respective effective volumes; and
provide said optimized control signals to at least one of said apparatus subsystems during said scan.

* * * * *